(12) United States Patent
Dewey et al.

(10) Patent No.: US 11,266,514 B2
(45) Date of Patent: *Mar. 8, 2022

(54) RADIOLUCENT TRIAL

(71) Applicant: Warsaw Orthopedic, Inc., Warsaw, IN (US)

(72) Inventors: Jonathan M. Dewey, Memphis, TN (US); William D. Armstrong, Memphis, TN (US); Anthony J. Melkent, Germantown, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 87 days.

This patent is subject to a terminal disclaimer.

(21) Appl. No.: 16/731,156

(22) Filed: Dec. 31, 2019

(65) Prior Publication Data

US 2020/0129313 A1 Apr. 30, 2020

Related U.S. Application Data

(63) Continuation of application No. 15/941,489, filed on Mar. 30, 2018, now Pat. No. 10,537,447.

(51) Int. Cl.
*A61F 2/46* (2006.01)

(52) U.S. Cl.
CPC .................. *A61F 2/4684* (2013.01)

(58) Field of Classification Search
CPC .......... A61F 2/44; A61F 2/4455; A61F 2/446; A61F 2/4465; A61F 2/447; A61F 2/46; A61F 2/4603; A61F 2/4611; A61F 2/4684
See application file for complete search history.

(56) References Cited

U.S. PATENT DOCUMENTS

| 6,723,097 B2 | 4/2004 | Fraser et al. |
| 7,763,078 B2 | 7/2010 | Peterman et al. |
| 7,776,049 B1 * | 8/2010 | Curran ..................... A61F 2/44 606/99 |

(Continued)

FOREIGN PATENT DOCUMENTS

WO 2013074419 5/2013

OTHER PUBLICATIONS

International Search Report and Written Opinion for PCT/US2019/024235, the counterpart application dated Jul. 8, 2019, 10 pages.

(Continued)

*Primary Examiner* — Eric S Gibson

(57) ABSTRACT

Spinal implant trials are provided having various configurations and sizes that aid the selection of spinal implants having similar configurations and sizes. A surgeon during surgery can insert various configurations and sizes of the spinal implant trials into a disc space between two adjacent vertebral bodies of a patient to enable the selection of a spinal implant configured and sized to fit the patient's disc space. Fluoroscopic images can be used in aiding the selection of an appropriately configured and sized spinal implant corresponding to one of the spinal implant trials. The spinal implant trials include features that reveal on the fluoroscopic images whether the spinal implant trials are properly located and oriented in the disc space and include features corresponding to different sizes of spinal implants also revealed on the fluoroscopic images.

20 Claims, 10 Drawing Sheets

(56) References Cited

U.S. PATENT DOCUMENTS

| | | | |
|---|---|---|---|
| 7,905,866 B2 | 3/2011 | Curran | |
| 7,905,886 B1 * | 3/2011 | Curran | A61F 2/4611 606/99 |
| 8,308,805 B2 * | 11/2012 | Lynn | A61F 2/447 623/17.16 |
| 8,623,088 B1 | 1/2014 | Tohmeh et al. | |
| 8,672,948 B2 | 3/2014 | Lemaitre | |
| 9,028,553 B2 * | 5/2015 | Lindenmann | A61F 2/4611 623/17.16 |
| 9,139,415 B2 | 9/2015 | Hall et al. | |
| 9,216,098 B2 | 12/2015 | Trudeau et al. | |
| 9,370,433 B1 | 6/2016 | Morris et al. | |
| 9,381,098 B2 | 7/2016 | Gittings et al. | |
| 9,693,882 B2 | 7/2017 | Lomeli et al. | |
| 9,730,802 B1 * | 8/2017 | Harvey | A61F 2/4611 |
| 9,895,236 B2 * | 2/2018 | Voellmicke | A61F 2/4611 |
| 10,537,447 B2 * | 1/2020 | Dewey | A61F 2/4684 |
| 2003/0139813 A1 | 7/2003 | Messerli et al. | |
| 2004/0162616 A1 * | 8/2004 | Simonton | A61F 2/4684 623/17.11 |
| 2004/0186572 A1 * | 9/2004 | Lange | A61F 2/4611 623/17.11 |
| 2006/0167461 A1 | 7/2006 | Hawkins et al. | |
| 2006/0217806 A1 * | 9/2006 | Peterman | A61F 2/447 623/17.11 |
| 2006/0217807 A1 * | 9/2006 | Peterman | A61F 2/4611 623/17.11 |
| 2007/0032872 A1 * | 2/2007 | Simonton | A61F 2/4611 623/17.11 |
| 2008/0262623 A1 * | 10/2008 | Bagga | A61F 2/442 623/17.16 |
| 2010/0076559 A1 * | 3/2010 | Bagga | A61F 2/4611 623/17.16 |
| 2010/0198263 A1 | 8/2010 | Siegal et al. | |
| 2011/0092976 A1 | 4/2011 | Rawles et al. | |
| 2011/0106261 A1 * | 5/2011 | Chin | A61F 2/4455 623/17.16 |
| 2012/0165945 A1 * | 6/2012 | Hansell | A61F 2/4465 623/17.16 |
| 2012/0232664 A1 * | 9/2012 | Ulrich, Jr. | A61F 2/4465 623/17.16 |
| 2012/0239150 A1 * | 9/2012 | Ullrich, Jr. | A61F 2/4465 623/17.16 |
| 2012/0239151 A1 * | 9/2012 | Ulrich, Jr. | A61F 2/4611 623/17.16 |
| 2014/0114421 A1 * | 4/2014 | Ullrich, Jr. | A61F 2/447 623/17.16 |
| 2014/0172103 A1 | 6/2014 | O'Neil et al. | |
| 2015/0100129 A1 | 4/2015 | Waugh et al. | |
| 2015/0112442 A1 * | 4/2015 | Foley | A61F 2/447 623/17.16 |
| 2015/0342757 A1 | 12/2015 | Lomeli et al. | |
| 2016/0120660 A1 | 5/2016 | Melkent | |
| 2016/0262909 A1 | 9/2016 | Lindenmann | |
| 2016/0270931 A1 * | 9/2016 | Trieu | A61F 2/30942 |
| 2017/0238984 A1 | 8/2017 | Kleiner | |
| 2017/0239067 A1 | 8/2017 | Nino | |
| 2018/0235778 A1 * | 8/2018 | Nino | A61B 17/7059 |
| 2019/0076266 A1 * | 3/2019 | Trudeau | A61F 2/4455 |
| 2019/0247197 A1 * | 8/2019 | Jagannathan | A61F 2/447 |
| 2019/0247203 A1 * | 8/2019 | Nino | A61F 2/30 |
| 2019/9247197 | 8/2019 | Jagannathan | |
| 2019/0298546 A1 * | 10/2019 | Dewey | A61F 2/4684 |
| 2020/0129313 A1 * | 4/2020 | Dewey | A61F 2/4684 |

OTHER PUBLICATIONS

Extended European Search Report for EP Application No. 19774789.2 dated Nov. 21, 2021.

* cited by examiner

RADIOLUCENT TRIAL

CROSS-REFERENCE TO RELATED APPLICATIONS

This application is a continuation of U.S. application Ser. No. 15/941,489, filed Mar. 30, 2018; all of which is incorporated herein by reference.

FIELD OF THE INVENTION

The present invention generally relates to a spinal implant trial. More particularly, the present invention relates to a spinal implant trial used to facilitate the selection of appropriately configured and sized interbody spinal fusion implants. More particularly, the present invention relates to a spinal implant trial including features that reveal on fluoroscopic images whether the spinal implant trial is properly located/oriented in the disc space.

DESCRIPTION OF THE PRIOR ART

Widespread use of interbody spinal fusion implants has been adopted to treat disease of and injuries to the spine. Typically, spinal implant trials are used during surgery to select an appropriately configured and sized spinal fusion implant. Such spinal implant trials correspond to the shapes and dimensions of the spinal fusions available for use. For example, differently shaped and dimensioned spinal implant trials can be sequentially inserted into the disc space during surgery to test for size. Thereafter, a correspondingly shaped and dimensioned spinal fusion implant can be selected for implantation. However, visualization of the disc space in which the interbody spinal fusion implant is to be implanted is limited during surgery. As such, fluoroscopy can be used at different intervals during surgery to determine the location of spinal implant trials in the disc space. Furthermore, the spinal implant trials can be equipped with radio-opaque and/or substantially radio-opaque markers that can aid the location determination. Nevertheless, oftentimes it is difficult to determine the location of such markers in the fluoroscopic images. Therefore, there is a need for a spinal implant trial configured to aid the determination of the location of radio-opaque and/or substantially radio-opaque markers on fluoroscopic images.

SUMMARY OF THE INVENTION

The present invention in one preferred embodiment contemplates a method of situating a spinal implant trial, the method including providing a spinal implant trial having a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, a first end wall portion positioned at or adjacent the first end of the body portion, an upper wall portion extending between the first end and the second end of the body portion, a lower wall portion extending between the first end and the second end of the body portion, a first interior portion formed between a portion of the first end wall portion and portions of the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first column and a second column provided in the first interior portion, the first column and the second column being at least in part radio opaque, each of the first column and the second column extending from at least adjacent the upper wall portion of the body portion to at least adjacent the lower wall portion of the body portion, the first column and the second column being positioned along the first mid-longitudinal axis, and the head portion including a first end, an opposite second end collocated with the distal second end of the spinal implant trial, a second mid-longitudinal axis extending through the first end and the second end of the head portion, and a second end wall portion positioned at least adjacent the distal second end of the spinal implant trial, the second end wall portion including and extending between a first end portion and a second end portion, the first end portion and the second end portion being spaced apart from one another, the first end portion of the second end wall portion being positioned proximate the first end of the head portion and the second end portion of the second end wall portion being positioned proximate the second end of the head portion, the first end portion and the second end portion of the second end wall portion each having a thickness greater than the remainder of the second end wall portion and being at least in part radio opaque; inserting the spinal implant trial into a disc space between an upper vertebral body and a lower vertebral body to contact a portion of the upper wall portion with a lower endplate of the upper vertebral body and to contact a portion of the lower wall portion with an upper endplate of the lower vertebral body; and locating and orientating the spinal implant trial in a first location and orientation so that a horizontal first distance between the first end wall portion and the first column in a first fluoroscopic image from a direct lateral direction, and a horizontal second distance between the first column and the second column in the first fluoroscopic image are respectively proportional to a third distance between the first end wall portion and the first column and a fourth distance between the first column and the second column along the first mid-longitudinal axis.

The present invention in another preferred embodiment contemplates a method of situating a spinal implant trial, the method including inserting a spinal implant trial from an at least partially posterior direction into a disc space between an upper vertebral body and a lower vertebral body, the spinal implant trial including a body portion and a head portion, the body portion having at least a first end, an opposite second end, a first mid-longitudinal axis extending through the first end and the second end, an upper wall portion, a lower wall portion, and a first end wall portion at or adjacent the first end of the body portion, and an interior portion extending therethrough that is open along a majority of a first lateral side and a second lateral side of the body portion, the interior portion being interrupted by a first column and a second column, and defined by at least the upper wall portion, the lower wall portion, and the first end wall portion, the first column and the second column each being at least in part radio opaque, the first column and the second column being spaced apart from one another along the first mid-longitudinal axis, and the head portion including at least a second end wall portion including and extending between a first end portion and a second end portion, the first end portion and the second end portion being at least in part radio opaque, the first end portion and the second end portion being spaced apart from one another, and each of the first end portion and the second end portion having a thickness greater than the remainder of the second end wall portion; contacting the upper wall portion of the body portion of the spinal implant trial with a lower end portion of the upper vertebral body and contacting the lower wall portion of the body portion of the spinal implant trial with an upper end portion of the lower vertebral body; positioning the spinal implant trial in a first location and orientation within the disc space such that a substantial majority of the spinal implant trial is on only one side of the sagittal plane dividing the disc space into a right lateral side and a left lateral side; producing a first fluoroscopic image from a direct lateral direction of the spinal implant trial in the first location and orientation within the disc space; producing a second fluoroscopic image from an anterior-posterior direction of the spinal implant trial in the first location orientation within the disc space; adjusting the location and orientation of the spinal implant trial to position the spinal implant trial in a second location and orientation so that the first end portion and the second end portion of the second end wall portion are positioned on opposite sides of the sagittal plane in a second fluoroscopic image from an anterior-posterior direction.

The present invention in yet another preferred embodiment contemplates a spinal implant trial including a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, an upper wall portion extending between the first end and the second end of the body portion, a lower wall portion extending between the first end and the second end, a first interior portion formed between the upper wall portion and the lower wall portion of the body portion, a first opening provided on a first lateral side of the body portion between the upper wall portion and the lower wall portion of the body portion and communicating with the first interior portion, a second opening provided on a second lateral side of the body portion between the upper wall portion and the lower wall portion of the body portion and communicating with the first interior portion, and at least a first column and a second column provided in the first interior portion and being positioned along the first mid-longitudinal axis, the first column and the second column each being at least in part radio opaque, the first column and the second column each extending from at least adjacent the upper wall portion to at least adjacent the lower wall portion; the head portion including a first end, an opposite second end collocated with the distal second end of the spinal implant trial, a second mid-longitudinal axis extending through the first end and the second end of the head portion, an upper wall portion extending between the first end and the second end of the head portion, a lower wall portion extending between the first end and the second end of the head portion, a second interior portion communicating with the first interior portion and formed between the upper wall portion and the lower wall portion of the head portion, and a second end wall portion positioned at least adjacent the distal second end of the spinal implant trial, the end wall portion including and extending between a first end portion and a second end portion, the first end portion and the second end portion being spaced apart from one another, the first end portion of the end wall portion being positioned proximate the first end of the head portion and the second end portion of the end wall portion being positioned proximate the second end of the head portion, the first end portion and the second end portion of the end wall portion each having a thickness greater than the remainder of the end wall portion and being at least in part radio opaque; where the spinal implant trial is configured for insertion into a disc space between an upper vertebral body and a lower vertebral body, and after insertion into the disc space, fluoroscopic imagery can be used from a direct lateral direction and an anterior-posterior direction to determine if the spinal implant trial is at least properly located and oriented in the disc space, the fluoroscopic imagery from the direct lateral direction showing that the spinal implant trial is properly located and oriented within the disc space when the first end portion and the second end portion are substantially aligned with one another, and the fluoroscopic imagery from the anterior-posterior direction showing that the spinal implant trial is properly positioned with respect to the lateral width of the disc space when the first end portion and the second end portion of the end wall portion are positioned on opposite sides of the sagittal plane.

DETAILED DESCRIPTION OF THE PREFERRED EMBODIMENT

Figure 1:
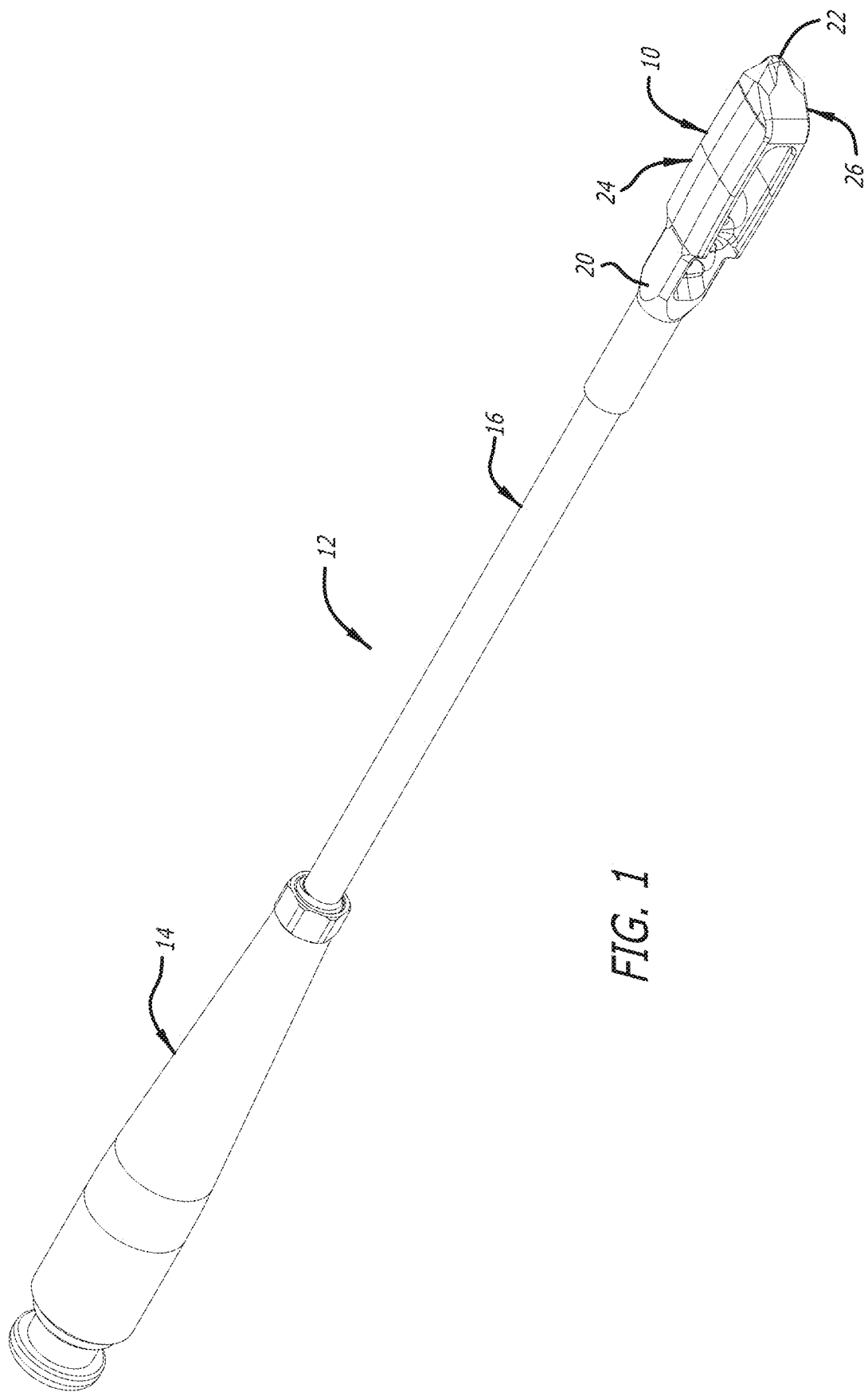
FIG. 1 is a top front perspective view of an instrument including a spinal implant trial according to a first embodiment of the present invention.
Figure 2:
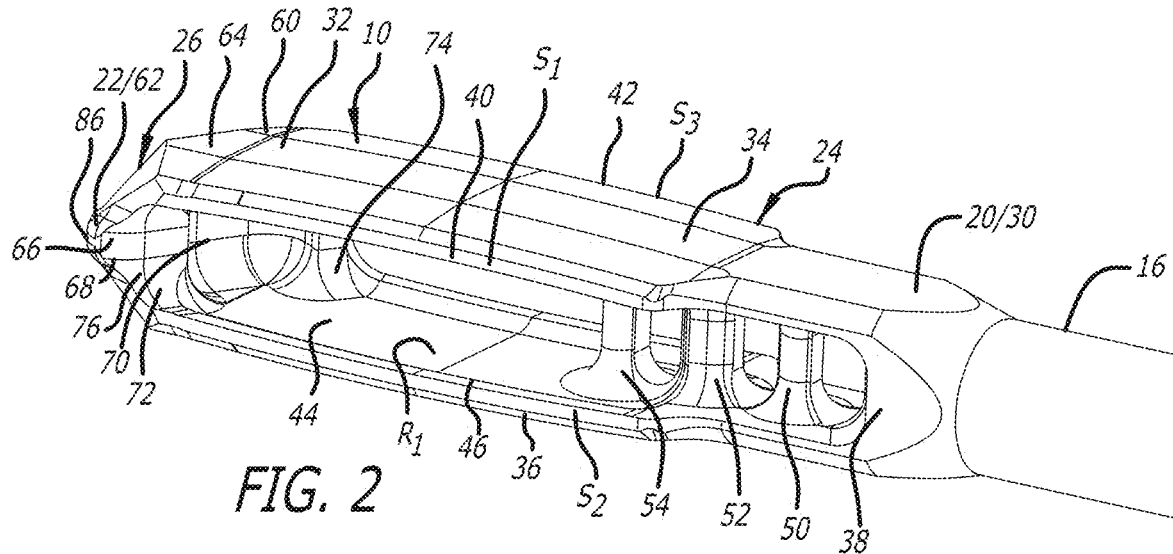
FIG. 2 is an enlarged top side perspective view of the spinal implant trial of FIG. 1.
Figure 3:
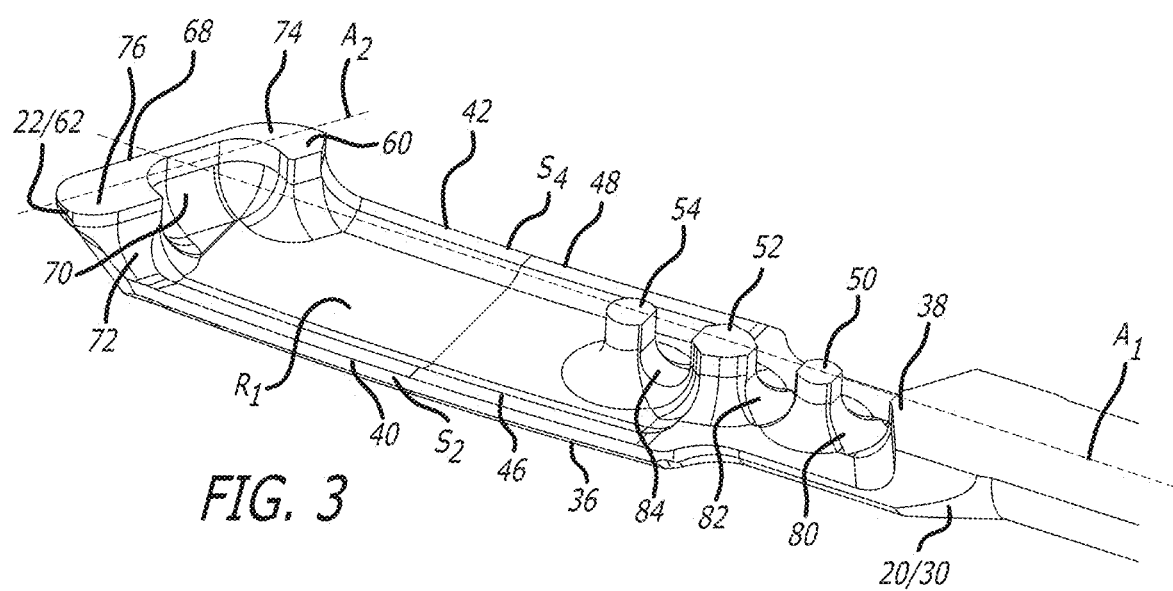
FIG. 3 is an enlarged cutaway view of FIG. 2 depicting the spinal implant trial of FIG. 1.

A spinal implant trial according to one embodiment of the present invention is generally referenced by the numeral 10 in FIGS. 1-3, a spinal implant trial according to another embodiment of the present invention is generally referenced by the number 110 in FIGS. 4-12, and a spinal implant trial according to yet another embodiment of the present invention is generally referenced by the number 240. The spinal implant trials 10, 110, and 240 can be formed of materials such as carbon steel, stainless steel, titanium, cobalt chrome, PEEK, tantalum, or any combination of these. The spinal implant trials 10, 110, and 240 can have various sizes corresponding to spinal implants having similar configurations and sizes. As such, a surgeon during surgery can insert various configurations and sizes of the spinal implant trials into a disc space between two adjacent vertebral bodies of a patient to enable the selection of a spinal implant configured and sized to fit the patient's disc space. As discussed below, the spinal implant trials 10, 110, and 240 can also include features that afford selection of appropriately-sized spinal implants.

Fluoroscopy is typically used throughout surgery to aid the selection of an appropriately configured and sized spinal implant. After insertion of one of the spinal implant trials 10, 110, and 240 into the disc space, a fluoroscope can be used to generate fluoroscopic images showing the position thereof in the disc space. Multiple fluoroscopic images from different directions can be generated periodically throughout the surgery to show advancement into and the position of the spinal implant trials 10, 110, and 240 in the disc space. For example, fluoroscopic images from anterior-posterior directions and fluoroscopic images from lateral directions can be generated.

The fluoroscopic images can be used in selecting an appropriately configured and sized spinal implant corresponding to one of the spinal implant trials 10, 110, and 240. Using the fluoroscopic images and the features thereof (such as, for example, one or more columns discussed below), the spinal implant trials 10, 110, and 240 can be properly located/oriented within the disc space. As such, the selection of the configuration and size, as well as ideal position in the disc space and implantation trajectory, of the spinal implant or spinal implants can be made after the spinal implant trials 10, 110, and 240 are properly located/oriented within the disc space.

As depicted in FIG. 1, the spinal implant trial 10 is included as part of an instrument 12, and the instrument 12 also has a handle 14 and a shaft 16. For example, the spinal implant trial 10 can be removably attached to the shaft 16, so that various sizes of the spinal implant trial 10 can be successively attached to the shaft 16. The surgeon can manipulate the spinal implant trial 10 into position within the disc space via manipulation of the handle 14.

The spinal implant trial 10, as depicted in FIGS. 2 and 3, includes a proximal first end 20 and a distal second end 22. A body portion 24 of the spinal implant trial 10 extends from the proximal first end 20 toward the distal second end 22, and a head portion 26 of the spinal implant trial 10 extends from the body portion 24 to the distal second end 22.

The body portion 24 includes a first end 30, an opposite second end 32, and a mid-longitudinal axis $A_1$ extending through the first end 30 and the second end 32. The first end 30 is collocated with the proximal first end 20, and the second end 32 is located adjacent the head portion 26. The body portion 24 includes an upper wall portion 34 and a lower wall portion 36 spaced apart from one another and extending between the first end 20 and the second end 32, and between a first lateral side 40 and a second lateral side 42 of the body portion 24. The body portion 24 further includes a first end wall portion 38 provided at and adjacent the first end 30. Portions of the upper wall portion 34 and the lower wall portion 36 can be convex, and the convexity can approximate the curvature of the end plates of the two adjacent vertebral bodies.

As depicted in FIG. 2, an interior 44 is formed between at least portions of the upper wall portion 34, the lower wall portion 36, and the first end wall portion 38. Furthermore, a first opening 46 into the interior 44 is formed between the upper wall portion 34 and the lower wall portion 36 at the first lateral side 40, and a second opening 48 into the interior 44 is formed between the upper wall portion 34 and the lower wall portion 36 at the second lateral side 42.

The first opening 46 and the second opening 48 serve as large "windows" into and through the interior 44. Much of the interior 44 is open space between the first lateral side 40 and the second lateral side 42, and as such, there is an uninterrupted view, both visually and fluoroscopically, through much of the interior 44 between the first lateral side 40 and the second lateral side 42. Alternatively, the interior 44 could be filled with a radiolucent material or substantially radiolucent material to fill in all or portions of the open space, and/or fill much (if not all) of the first opening 46 and the second opening 48. The presence of the radiolucent or substantially radiolucent material could be used to reinforce the upper wall portion 34 and the lower wall portion 36, and/or inhibit abrasion of tissues and inhibit tissues from entering the first opening 46 and the second opening 48. For example, the interior 44 could be filled with a radiolucent polymeric material, and the polymeric material could extend throughout the interior 44 and between the below-discussed one or more columns and/or the terminal portions of the interior 44. Furthermore, the space between the one or more columns and/or the terminal portions of the interior 44 also could be filled with a metallic material made thin enough to be substantially radiolucent.

The upper wall portion 34 and the lower wall portion 36 include side surfaces $S_1$ and $S_2$, respectively, along the first lateral side 40 of the body portion 24, and the upper wall portion 34 and the lower wall portion 36 include side surfaces $S_3$ and $S_4$, respectively, along the second lateral side 42 of the body portion 24. As depicted in FIG. 3, the lower wall portion 36 can include a recessed area $R_1$ that increases the dimensions of the interior 44. Although not shown, the upper wall portion 34 similarly can include a recessed area that increases the dimensions of the interior 44. The recessed areas formed in the upper wall portion 34 and the lower wall portion 36 provide for thinner portions of the upper wall portion 34 and the lower wall portion 36 to reduce their radiographic signature and effectively create lip portions on which the side surfaces $S_1$, $S_2$, $S_3$, and $S_4$ are formed. The size of the side surfaces $S_1$, $S_2$, $S_3$, and $S_4$ can serve in inhibiting tissues from entering the first opening 46 and the second opening 48 and reducing abrasion of the tissues thereon.

Portions (if not all) of the side surfaces $S_1$ and $S_2$ reside in a first plane extending parallel to the mid-longitudinal axis $A_1$, and portions (if not all) of the side surfaces $S_3$ and $S_4$ reside in a second plane extending parallel to the mid-longitudinal axis $A_1$. Substantially all (if not all) of the body portion 24 and the head portion 26 reside between the first and second planes.

As depicted in FIGS. 2 and 3, one or more columns are provided in the interior 44. For example, a first column 50 is provided in the interior 44 at and adjacent the first end 30 of the body portion 24, a second column 52 is provided in the interior 44 adjacent the first column 50, and a third column 54 is provided in the interior 44 adjacent the second column 52.

In a preferred embodiment of the invention, the first, second, and third columns 50, 52, and 54 can be formed of different shapes and can have different dimensions provided at least that the columns substantially extend along the mid-longitudinal axis $A_1$ of the body portion 124 and the columns are distinguishable from one another. As depicted FIGS. 2 and 3, the first column 50, the second column 52, and the third column 54 are substantially cylindrical, and the first column 50 and the third column 54 have smaller dimensions along the mid-longitudinal axis $A_1$ than the dimension of the second column 52 along the mid-longitudinal axis $A_1$. The first column 50, the second column 52, and the third column 54 can also have different shapes with cross-sections such as, for example, squares, rectangles, trapezoids, parallelograms, pentagons, and/or octagons. The first column 50, the second column 52, and the third column 54 extend from at least adjacent the upper wall portion 34 to at least adjacent the lower wall portion 36. Furthermore, the first column 50, the second column 52, and the third column 54, for example, can be created via machining processes during manufacturing or formed by additive manufacturing processes. As depicted in FIG. 3, the upper bases and lower bases of the first column 50, the second column 52, and the third column 54 include curved transitions or corner rounds into the remainder of the spinal implant trial 10. These transitions may be necessitated by the limitations of machining during manufacturing. However, more abrupt transitions of the first column 50, the second column 52, the third column 54 into the remainder of the spinal implant trial 10 may be desirable and could, for example, be created using additive manufacturing processes. The abrupt transitions could aid in better visualization of the first column 50, the second column 52, and the third column 54. As discussed below, the first column 50, the second column 52, and the third column 54 can be used in properly locating/orienting the spinal implant trial 10 in the disc space, and the first column 50, the second column 52, and the third column 54 can be used in selecting an appropriately sized spinal implant.

While the first column 50, the second column 52, and the third column 54 are provided along the mid-longitudinal axis $A_1$ in FIG. 3, additional and/or substitute columns could be provided along a multiple of different axes in other preferred embodiments. Like the use of the first column 50, the second column 52, and the third column 54, the selection of additional and/or substitute columns and different axes can be made to facilitate the discernibility of the shape, length, location, and/or trajectory of the trial and the spinal implant or spinal implants ultimately used.

The first column 50, the second column 52, and the third column 54 can be formed integrally with and of the same material as the remainder of the spinal implant trial 10. Portions of the first column 50, the second column 52, and the third column 54 could be radio-opaque or substantially radio-opaque or gradations thereof. Also, in addition to portions thereof being radio-opaque or substantially radio-opaque, portions of the first column 50, the second column 52, and the third column 54 could be radiolucent or substantially radiolucent. For example, the center portions of the first column 50, the second column 52, and the third column 54 could be radiolucent and the remainder thereof could be radio-opaque or substantially radio-opaque. Also, as metals become thinner, their radiolucency increases, and thus, the geometries and the thickness of the geometries of the columns could be adjusted to give the desired radiolucency. This radiolucency could be in a specific area using sharp transitions between thick and thin areas to give a clear indication of shape, length, location, and/or trajectory of the trial and the spinal implant or spinal implants ultimately used.

The head portion 26 includes a first end 60, an opposite second end 62, and a mid-longitudinal axis $A_2$ extending through the first end 60 and the second end 62. The first end 60 is collocated with a portion of the second end 32 of the body portion 24, and the second end 62 is collocated with the distal second end 22. The mid-longitudinal axis $A_2$ is transverse to the mid-longitudinal axis $A_1$.

The head portion 26 includes an upper wall portion 64, a lower wall portion 66, and a second end wall portion 68. The upper wall portion 64 can be formed contiguously and continuously with the upper wall portion 34, and the lower wall portion 66 can be formed contiguously and continuously with the lower wall portion 36. The upper wall portion 64 and the lower wall portion 66 are spaced apart from one another and extend between the first end 60 and the second end 62, and between the second end 32 of the body portion 24 and the second end wall portion 68.

As depicted in FIG. 3, an interior 70 is formed between the upper wall portion 64 and the lower wall portion 66. Furthermore, the interior 70 is bordered in part by the second end wall portion 68, and the interior 70 is contiguous and continuous with the interior 44 of the body portion 24. Like much of the interior 44, the interior 70 can be open space, or alternatively, the interior 70 can be filled with a radiolucent material. An opening 72 into the interior 70 is formed adjacent the second end 62 of the head portion 26. The opening 72 is formed adjacent the first lateral side 40 of the body portion 24, and the opening 72 can be contiguous and continuous with the opening 46.

The second end wall portion 68 includes a first end portion 74 proximate the first end 60 of the head portion 26 and a second end portion 76 proximate the second end 62 of the head portion 26. The first end portion 74 protrudes into portions of the interior 44 and the interior 70, and the second end portion 76 protrudes into portions of the interior 70. The first end portion 74 and the second end portion 76 each have a thickness greater than the remainder of the second end wall portion 68. The first end portion 74 and the second end portion 76 can be radio-opaque or substantially radio-opaque. Furthermore, when aligned with one another, the first end portion 74 and the second end portion 76 have approximately the same shape.

As discussed in detail with respect to similar features of the spinal implant trial 110, the first column 50, the second column 52, the third column 54, and the second end wall portion 68 can be used to determine whether the spinal implant trial 10 is properly located/oriented. Furthermore, when the spinal implant trial 10 is properly located/oriented, the distances between the first end wall portion 38, and the first column 50, the second column 52, and/or the third column 54 can be used to select appropriately sized spinal implants.

In the corresponding portions of the interior 44, a first space 80 is formed between the first end wall portion 38 and the first column 50, a second space 82 is formed between the first column 50 and the second column 52, and a third space 84 is formed between the second column 52 and the third column 54. Because the first space 80, the second space 82, and the third space 84 are devoid of any interfering material or filled with a radiolucent or substantially radiolucent material, the locations of the first column 50, the second column 52, and the third column 54 can be clearly seen in fluoroscopic imagery. As discussed in detail with respect to similar features of the spinal implant trial 110, the locations of the first column 50, the second column 52, and the third column 54, the first end portion 74, and the second end portion 76 can be used to select appropriately sized spinal implants.

The head portion 26 at and adjacent the second end 62 thereof includes an exterior surface 86 that facilitates entry of the spinal implant trial 10 into the disc space. The exterior surface 86 can be formed as a nose portion similar to that disclosed in U.S. Ser. No. 15/818,395, filed Nov. 20, 2017, which is hereby incorporated by referenced in its entirety.

Figure 4:
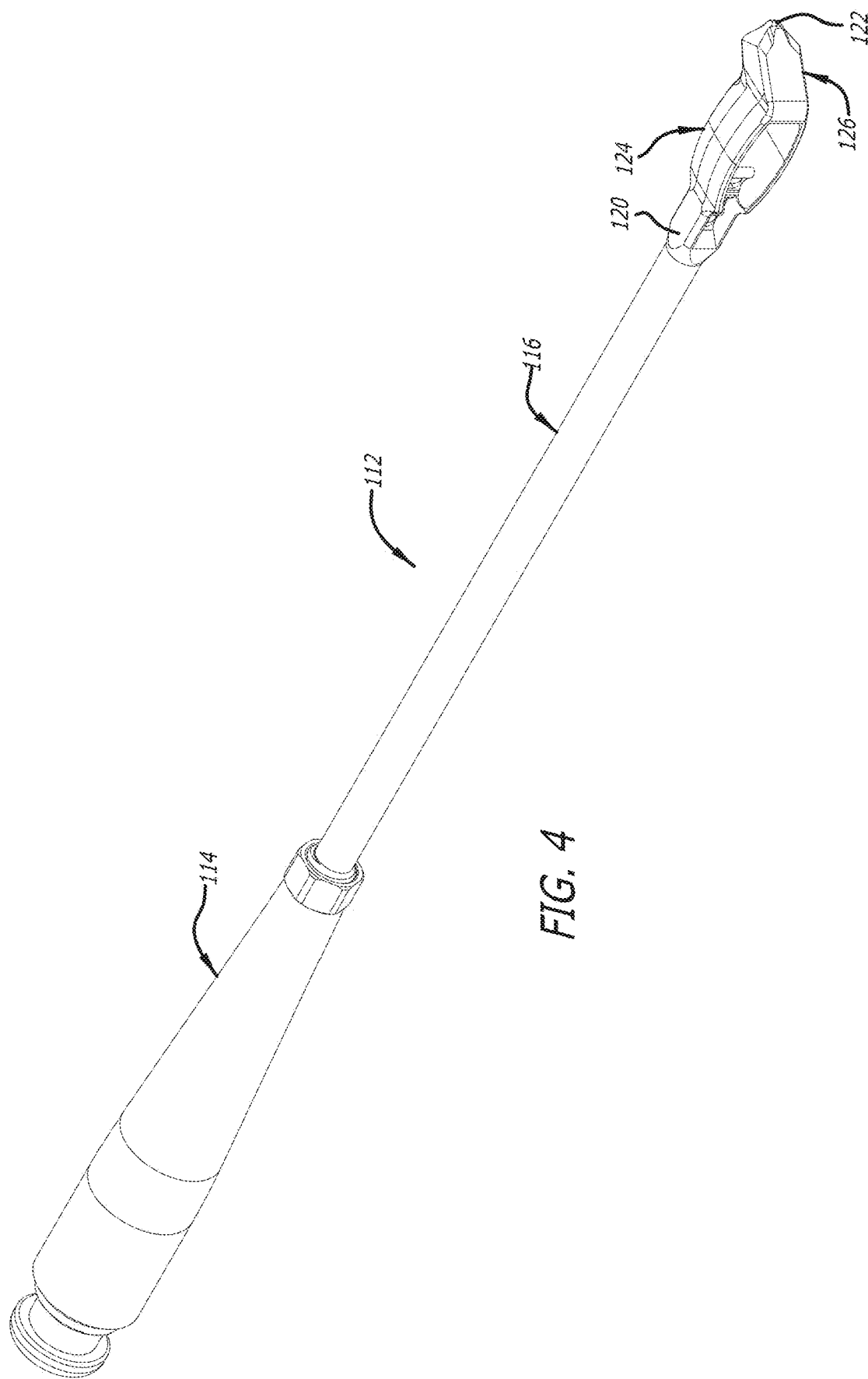
FIG. 4 is a top front perspective view of an instrument including a spinal implant trial according to a second embodiment of the present invention.

As depicted in FIG. 4, the spinal implant trial 110 is included as part of an instrument 112, and the instrument 112 also has a handle 114 and a shaft 116. For example, the spinal implant trial 110 can be removably attached to the shaft 116, so that various sizes of the spinal implant trial 110 can be successively attached to the shaft 116. The surgeon can manipulate the spinal implant trial 110 into position within the disc space via manipulation of the handle 114.

Figure 5:
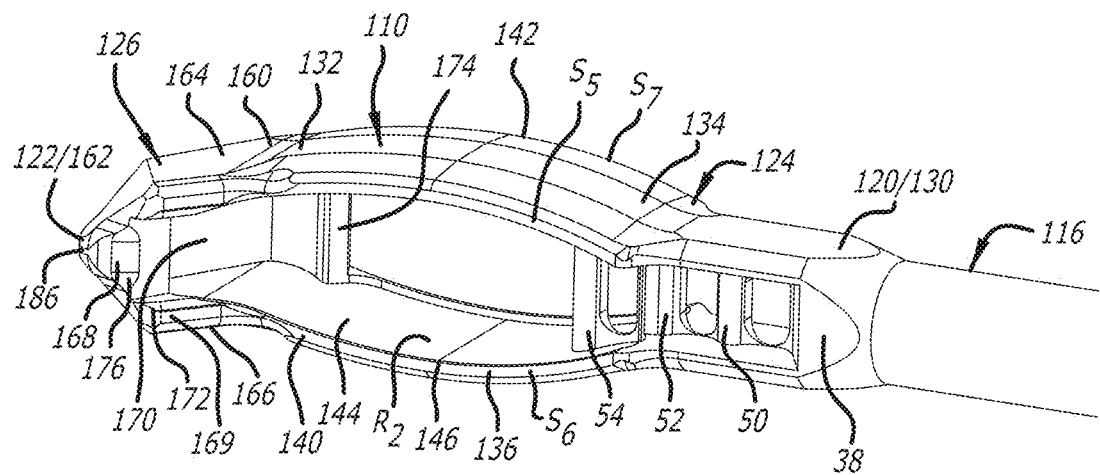
FIG. 5 is an enlarged top side perspective view of the spinal implant trial of FIG. 4.
Figure 6:
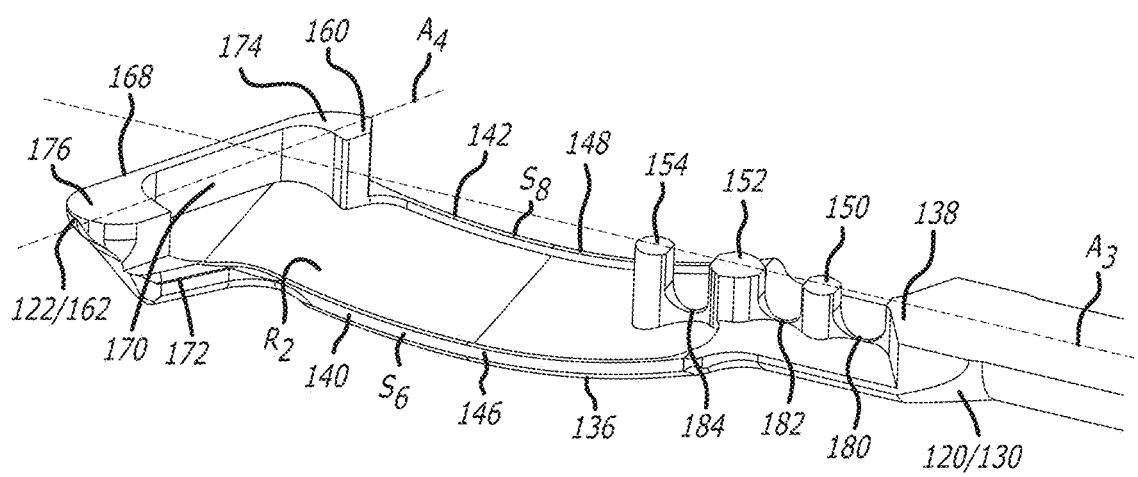
FIG. 6 is an enlarged cutaway view of FIG. 5 depicting the spinal implant trial of FIG. 4.

The spinal implant trial 110, as depicted in FIGS. 5 and 6, includes a proximal first end 120 and a distal second end 122. A body portion 124 of the spinal implant trial 110 extends from the proximal first end 120 toward the distal second end 122, and a head portion 126 of the spinal implant trial 110 extends from the body portion 124 to the distal second end 122. As discussed below, unlike the head portion 26 of the spinal implant trial 10, the head portion 126 of the spinal implant trial 110 is extended relative to the body portion 124

The body portion 124 includes a first end 130, an opposite second end 132, and mid-longitudinal axis $A_3$ extending through the first end 130 and the second end 132. The first end 130 is collocated with the proximal first end 120, and the second end 132 is located adjacent the head portion 126. The body portion 124 includes an upper wall portion 134 and a lower wall portion 136 spaced apart from one another and extending between the first end 130 and the second end 132, and between a first lateral side 140 and a second lateral side 142 of the body portion 124. The body portion 124 further includes a first end wall portion 138 provided at and adjacent the first end 130. Portions of the upper wall portion 134 and the lower wall portion 136 can be convex, and the convexity can approximate the curvature of the end plates of the two adjacent vertebral bodies.

As depicted in FIG. 5, an interior 144 is formed between at least portions of the upper wall portion 134, the lower wall portion 136, and the first end wall portion 138. Furthermore, a first opening 146 into the interior 144 is formed between the upper wall portion 134 and the lower wall portion 136 at the first lateral side 140, and a second opening 148 into the interior 144 is formed between the upper wall portion 134 and the lower wall portion 136 at the second lateral side 142.

The first opening 146 and the second opening 148 serve as large "windows" into and through the interior 144. Much of the interior 144 is open space between the first lateral side 140 and the second lateral side 142, and as such, there is an uninterrupted view, both visually and fluoroscopically, through much of the interior 144 between the first lateral side 140 and the second lateral side 142. Alternatively, the interior 144 could be filled with radiolucent material or substantially radiolucent material to fill in all or portions of the open space, and/or fill much (if not all) of the first opening 146 and the second opening 148. The presence of the radiolucent or substantially radiolucent material could be used to reinforce the upper wall portion 134 and the lower wall portion 136, and inhibit abrasion of tissues and inhibit tissues from entering the first opening 146 and the second opening 148. For example, the interior 144 could be filled with a radiolucent polymeric material, and the polymeric material could extend throughout the interior 144 and between the below-discussed one or more columns and/or the terminal portions of the interior 144. Furthermore, the space between the one or more columns and/or the terminal portions of the interior 144 also could be filled with a metallic material made thin enough to be substantially radiolucent.

The upper wall portion 134 and the lower wall portion 136 include side surfaces $S_5$ and $S_6$, respectively, along the first lateral side 140 of the body portion 124, and the upper wall portion 134 and the lower wall portion 136 include side surfaces $S_7$ and $S_8$, respectively, along the second lateral side 142 of the body portion 124. As depicted in FIG. 5, the lower wall portion 136 can include a recessed area $R_2$ that increases the dimensions of the interior 144. Although not shown, the upper wall portion 134 similarly can include a recessed area that increases the dimensions of the interior 144. The recessed areas formed in the upper wall portion 134 and the lower wall portion 136 provide for thinner portions of the upper wall portion 134 and the lower wall portion 136 to reduce their radiographic signature and effectively create lip portions on which the side surfaces $S_5$, $S_6$, $S_7$, and $S_8$ are formed. The size of the side surfaces can serve in inhibiting tissues from entering the first opening 146 and the second opening 148 and reducing abrasion of the tissue thereon.

Portions (if not all) of the side surfaces $S_5$ and $S_6$ reside in a third plane extending parallel to the mid-longitudinal axis $A_3$, and portions (if not all) of the side surfaces $S_7$ and $S_8$ reside in a fourth plane extending parallel to the mid-longitudinal axis $A_3$. Substantially all (if not all) of the body portion 124 and portions of the head portion 126 reside between the third and fourth planes.

As depicted in FIGS. 5 and 6, one or more columns are provided in the interior 144. For example, a first column 150 is provided in the interior 144 at and adjacent the first end 130 of the body portion 124, a second column 152 is provided in the interior 144 adjacent the first column 150, and a third column 154 is provided in the interior 144 adjacent the second column 152.

In a preferred embodiment of the invention, the first, second, and third columns 150, 152, and 154 can be formed of different shapes and can have different dimensions provided at least that the columns substantially extend along the mid-longitudinal axis $A_3$ of the body portion 124 and the columns are distinguishable from one another. As depicted in FIGS. 5 and 6, the first column 150, the second column 152, and the third column 154 are substantially cylindrical, and the first column 150 and the third column 154 have smaller dimensions along the mid-longitudinal axis $A_1$ than the dimensions of the second column 152 along the mid-longitudinal axis $A_1$. The first column 150, the second column 152, and the third column 154 can also have different shapes with cross-sections such as, for example, squares, rectangles, trapezoids, parallelograms, pentagons, and/or octagons. The first column 150, the second column 152, and the third column 154 extend from at least adjacent the upper wall portion 134 to at least adjacent the lower wall portion 136. Furthermore, the first column 150, the second column 152, and the third column 154, for example, can be created via machining processes during manufacturing or formed by additive manufacturing processes. As depicted in FIG. 3, the upper bases and lower bases of the first column 150, the second column 152, and the third column 154 include abrupt transitions into the remainder of the spinal implant trial 110. These abrupt transitions may be desirable and could, for example, be created using additive manufacturing processes. The abrupt transitions could aid in better visualization of the first column 150, the second column 152, and the third column 154. The first column 150, the second column 152, and the third column 154 can be used in properly locating/orienting the spinal implant trial 110 in the disc space, and the first column 150, the second column 152, and the third column 154 can be used in selecting an appropriately sized spinal implant.

While the first column 150, the second column 152, and the third column 154 are provided along the mid-longitudinal axis $A_3$ in FIG. 6, additional and/or substitute columns could be provided along a multiple of different axes in other preferred embodiments. Like the use of the first column 150, the second column 152, and the third column 154, the selection of additional and/or substitute columns and different axes can be made to facilitate the discernibility of the shape, length, location, and/or trajectory of the trial and the spinal implant or spinal implants ultimately used.

The first column 150, the second column 152, and the third column 154 can be formed integrally with and of the same material as the remainder of the spinal implant trial 110. Portions of the first column 150, the second column 152, and the third column 154 could be radio-opaque or substantially radio-opaque or gradations thereof. Also, in addition to portions thereof being radio-opaque or substantially radio-opaque, portions of the first column 150, the second column 152, and the third column 154 could be radiolucent or substantially radiolucent. For example, the center portions of the first column 150, the second column 152, and the third column 154 could be radiolucent and the remainder thereof could be radio-opaque or substantially radio-opaque. Also, as metals become thinner, their radiolucency increases, and thus, the geometries and the thickness of the geometries of the columns could be adjusted to give the desired radiolucency. This radiolucency could be in a specific area using sharp transitions between thick and thin areas to give a clear indication of shape, length, location, and/or trajectory of the trial and the spinal implant or spinal implants ultimately used.

The head portion 126 includes a first end 160, an opposite second end 162, and a mid-longitudinal axis $A_4$ extending through the first end 160 and the second end 162. The first end 160 is collocated with a portion of the second end 132 of the body portion 124, and the second end 162 is collocated with the distal second end 122. The mid-longitudinal axis $A_3$ is transverse to the mid-longitudinal axis $A_4$.

The head portion 126 includes an upper wall portion 164, a lower wall portion 166, a second end wall portion 168, and a sidewall portion 169. The upper wall portion 164 can be formed contiguously and continuously with the upper wall portion 134, and the lower wall portion 166 can be formed contiguously and continuously with the lower wall portion 136. The upper wall portion 164 and the lower wall portion 166 are spaced apart from one another and extend between the first end 160 and the second end 162, and between the second end 132 of the body portion 124, the second end wall portion 168, and the sidewall portion 169. Unlike the head portion 26 of the spinal implant trial 10, a portion of the head portion 126 extends beyond the third plane. The extended head portion 126 makes the spinal implant trial 110 resemble a hockey-stick.

As depicted in FIG. 6, an interior 170 is formed between the upper wall portion 164 and the lower wall portion 166. Furthermore, the interior 170 is bordered in part by the second end wall portion 168, and the interior 170 is contiguous and continuous with the interior 144 of the body portion 124. Like much of the interior 144, the interior 170 can be open space, or alternatively, the interior 170 can be filled with a radiolucent material. An opening 172 into the interior 170 is formed adjacent the second end 162 of the head portion 126. The opening 172 is formed adjacent the first lateral side 140 of the body portion 124, and the opening 172 can be contiguous and continuous with the first opening 146.

Figure 9:
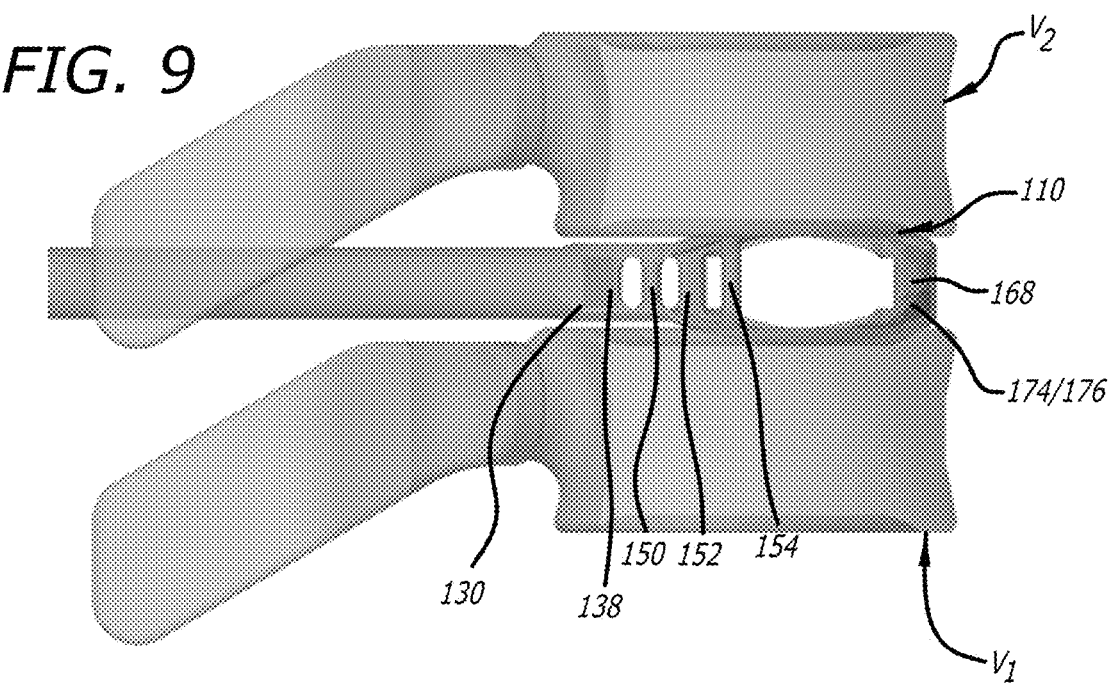
FIG. 9 is a representation of a direct lateral fluoroscopic image of the spinal implant trial of FIG. 4 in the first position in the disc space.

The second end wall portion 168 includes a first end portion 174 proximate the first end 160 of the head portion 126 and a second end portion 176 proximate the second end 162 of the head portion 126. The first end portion 174 protrudes into portions of the interior 144 and the interior 170, and the second end portion 176 protrudes into portions of the interior 170. The first end portion 174 and the second end portion 176 each have a thickness greater than the remainder of the second end wall portion 168. The first end portion 174 and the second end portion 176 can be radio-opaque or substantially radio-opaque. Furthermore, when aligned with one another, the first end portion 174 and the second end portion 176 have approximately the same shape (FIG. 9).

The first column 150, the second column 152, the third column 154, and the second end wall portion 168 can be used to determine whether the spinal implant trial 110 is properly located/oriented. Furthermore, when the spinal implant trial 110 is properly located/oriented, the distances between the first end wall portion 138, and the first column 150, the second column 152, and/or the third column 154 can be used to select appropriately sized spinal implants.

In the corresponding portions of the interior 144, a first space 180 is formed between the first end wall portion 138 and the first column 150, a second space 182 is formed between the first column 150 and the second column 152, and a third space 184 is formed between the second column 152 the third column 154. Because the first space 180, the second space 182, and the third space 184 are devoid of any interfering material or filled with a radiolucent or substantially radiolucent material, the locations of the first column 150, the second column 152, and the third column 154 can be clearly seen in fluoroscopic imagery. The locations of the first column 150, the second column 152, and the third column 154, the first end portion 174, and the second end portion 176 can be used to select appropriately sized spinal implants.

The head portion 126 at and adjacent the second end 162 thereof includes an exterior surface 186 that facilitates entry of the spinal implant trial 110 into the disc space. The exterior surface 186 can be formed as a nose portion like the nose portion 86.

Figure 7:
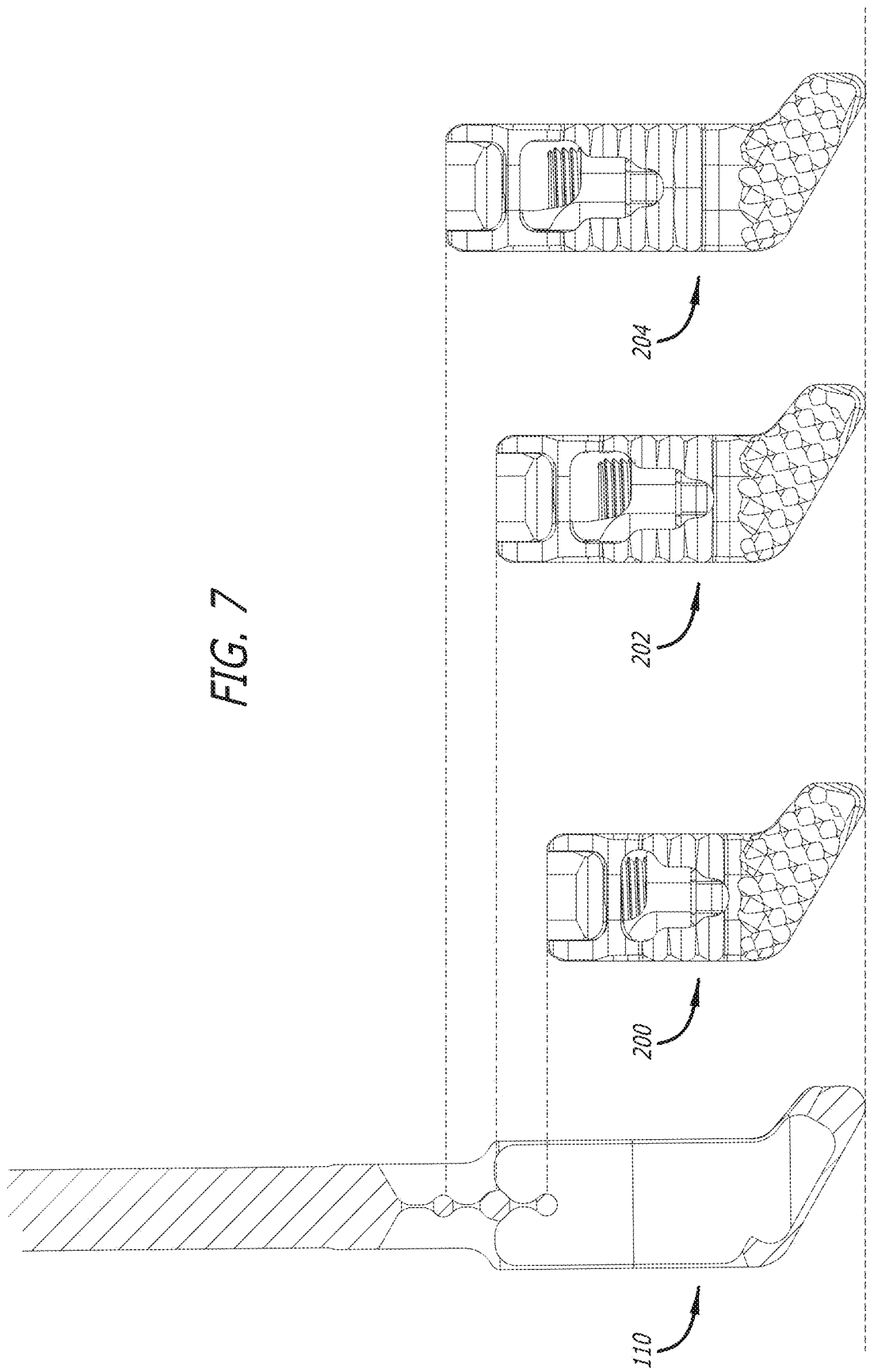
FIG. 7 is top plan view of the spinal implant trial of FIG. 4 and three sizes of spinal implants for which the spinal implant trial is used to facilitate selection thereof.

FIG. 7 depicts a portion of the spinal implant trial 110 showing the first column 150, the second column 152, and the third column 154 adjacent a first spinal implant 200, a second spinal implant 202, and a third spinal implant 204. The first spinal implant 200, the second spinal implant 202, and the third spinal implant 204 have similar configurations to the spinal implant trial 110. As depicted in FIG. 7, the placement of the first column 150 corresponds to the size of the first spinal implant 200, the placement of the second column 152 corresponds to the size of the second spinal implant 202, and the placement of the third column 154 corresponds to the size of the third spinal implant 204. The first column 50, the second column 52, and the third column 54 of the spinal implant trial 10 are similarly arranged to correspond to sizes of spinal implants (not shown) having similar configurations as the spinal implant trial 10. As such, when the spinal implant trials 10 and 110 are properly located/oriented within the disc space, the proper size of a spinal implant to be used can be determined using the first column 50, the second column 52, and the third column 54, and using the first column 150, the second column 152, and the third column 154. For example, once the spinal implant trials 10 and 110 are properly located/oriented, a surgeon could select a spinal implant having a length corresponding to the one of the first column 50, the second column 52, or the third column 54 or the one of the first column 150, the second column 152, or the third column 154 that is at or adjacent the posterior rims of the vertebral bodies.

The spinal implant trials 10 and 110 can be used in a variety of spinal procedures to facilitate the selection of the configuration and size, as well as ideal position in the disc space and implantation trajectory, of the spinal implant or spinal implants ultimately used. For example, the spinal implant trials 10 and 110 can be used in TLIF (tranforminal lumbar interbody fusion) and PLIF (posterior lumbar interbody fusion) procedures, and the geometry of the columns affords visualization of the shape, length, location, and/or trajectory of the trial and the spinal implant or spinal implants ultimately used in these procedures.

Figure 8:
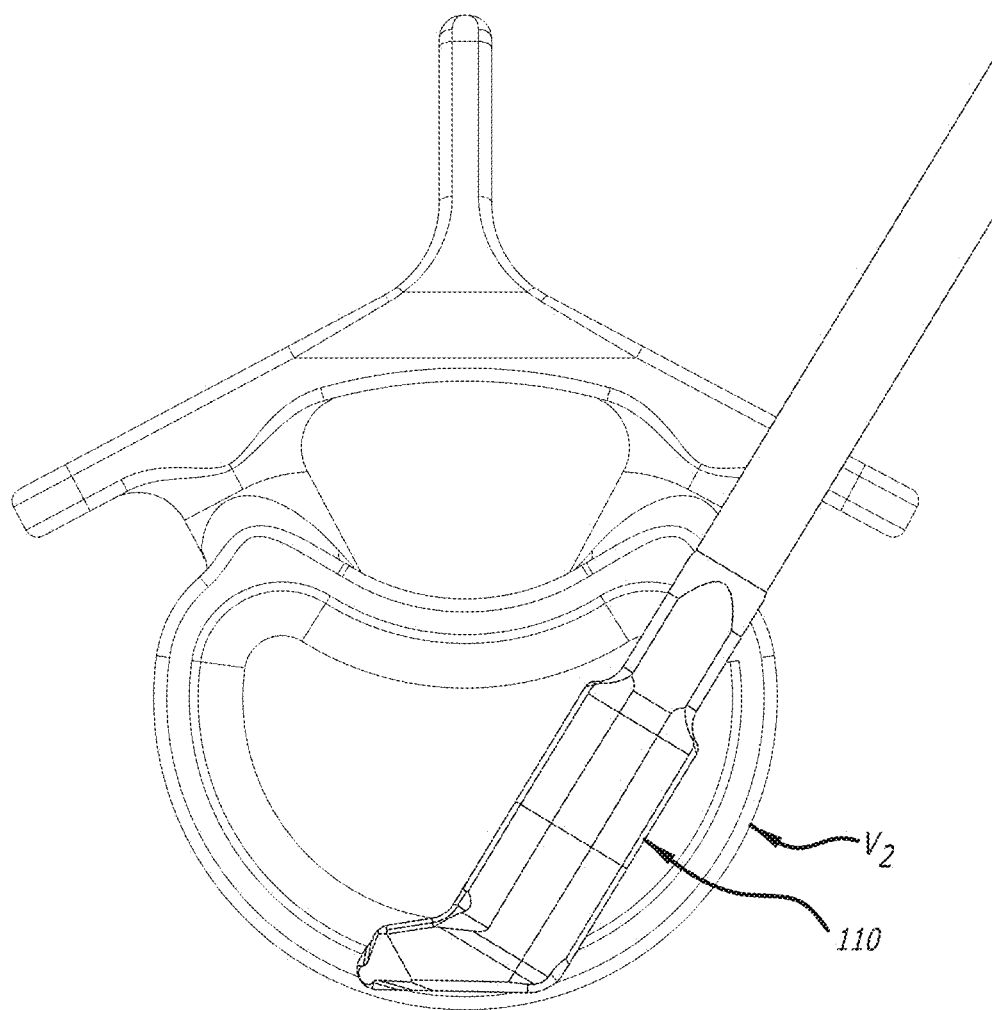
FIG. 8 is a top plan view of the spinal implant trial of FIG. 4 and a lower vertebral body bordering a disc space depicting the spinal implant trial in a first position after insertion thereof into the disc space.
Figure 10:
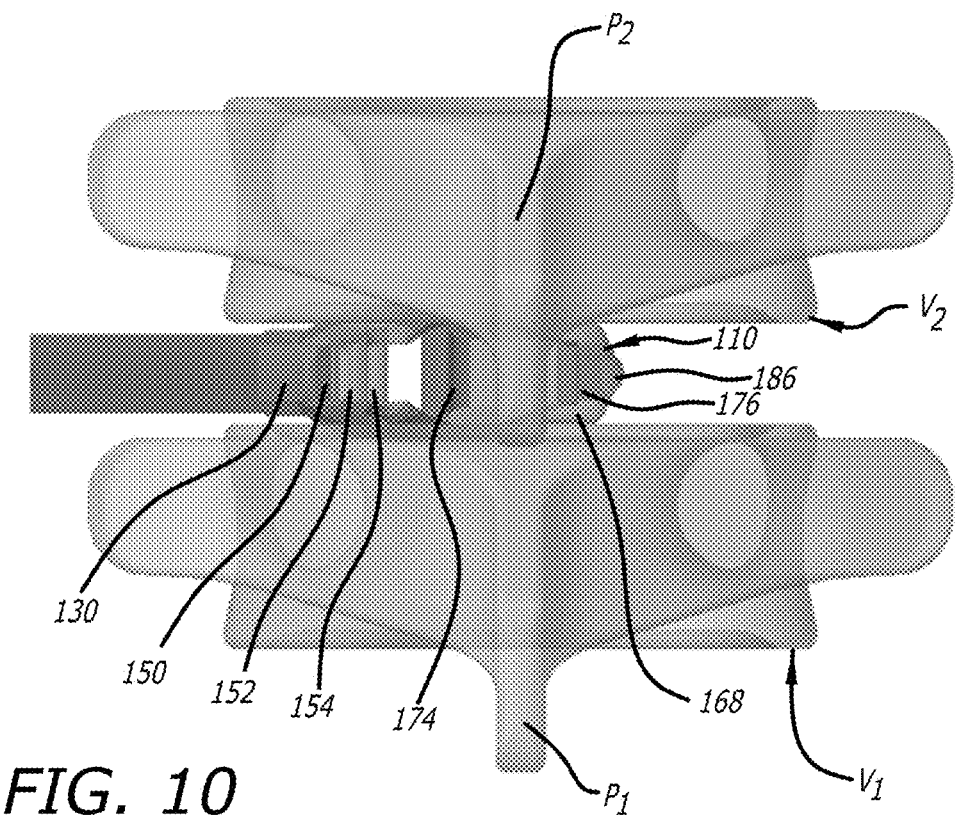
FIG. 10 is a representation of an anterior-posterior fluoroscopic image of the spinal implant trial of FIG. 4 in the first position in the disc space.
Figure 11:
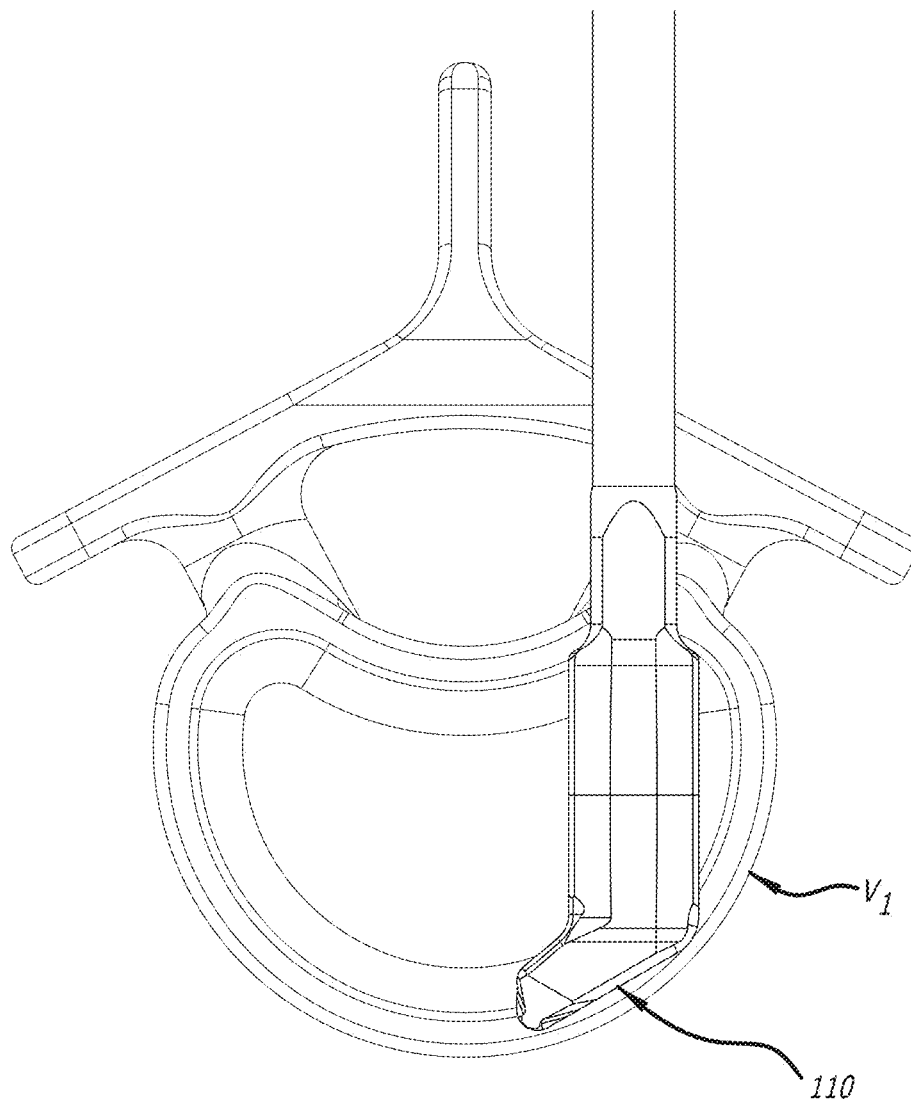
FIG. 11 is a top plan view of the spinal implant trial of FIG. 4 and the lower vertebral body bordering the disc space depicting the spinal implant trial in a second position after insertion thereof into the disc space.
Figure 12:
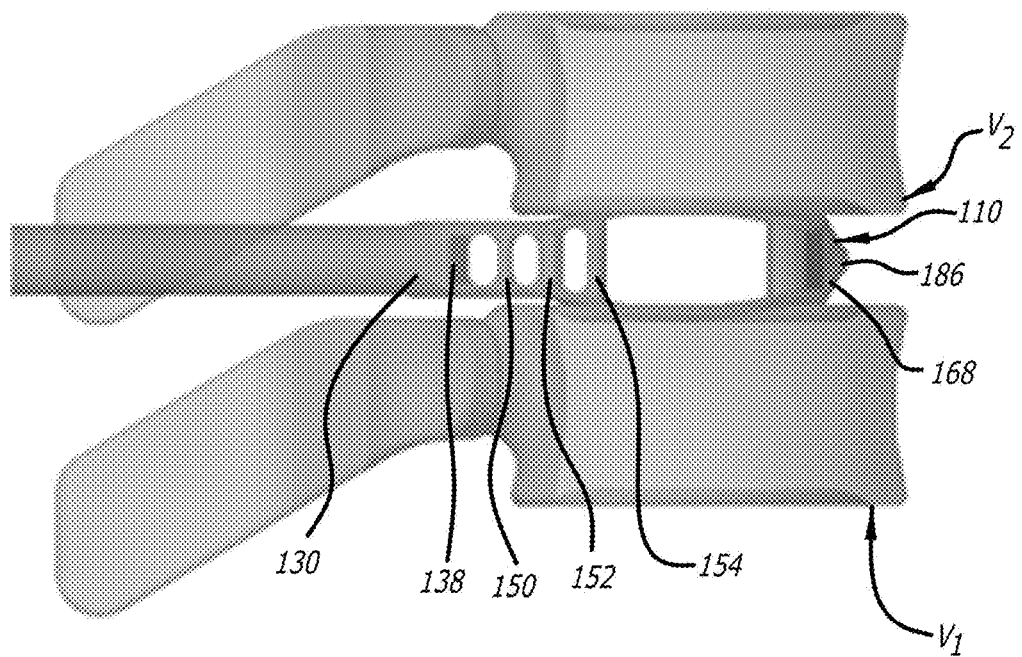
FIG. 12 is a representation of a direct lateral fluoroscopic image of the spinal implant trial of FIG. 4 in the second position in the disc space

To illustrate, FIGS. 8-10 show the position of the spinal implant trial 110 for a TLIF procedure, and FIGS. 11 and 12 show the position of the spinal implant trial 110 for a PLIF procedure. Once positioned in the disc space, as discussed below, fluoroscopy and the features of the spinal implant trial 110 can be used to determine whether the spinal implant trial 110 is properly located/oriented in the disc space between the lower vertebral body $V_1$ and the upper vertebral body $V_2$. After the initial insertion depicted in FIGS. 8 and 11, the spinal implant trial 110 can be positioned and repositioned to provide for the proper location/orientation thereof as determined by fluoroscopy and the features of the spinal implant trial 110. For example, fluoroscopy, images taken from lateral and/or anterior-posterior directions (FIGS. 9, 10, and 12) and the features of the spinal implant trial 110 depicted in the fluoroscopic images can be used to determine whether the spinal implant trial 110 is properly located/oriented in the disc space between the lower vertebral body $V_1$ and an upper vertebral body $V_2$. Thereafter, the features of the spinal implant trial 110 can be used to select the configuration and size, as well as ideal position in the disc space and implantation trajectory, of the spinal implant or spinal implants ultimately used.

FIGS. 9 and 10 are representations of fluoroscopic images taken of the spinal implant trial 110 as positioned in the disc space as shown FIG. 8 from the lateral direction and the anterior-posterior direction, respectively. FIGS. 9 and 10 show that the spinal implant trial 110 is properly located/oriented within the disc space for a TLIF procedure between the lower vertebral body $V_1$ and the upper vertebral body $V_2$.

When properly located/oriented, the lateral direction fluoroscopic representation depicted in FIG. 9 at the very least does not show the tip of the nose portion 186, shows the first end portion 174 and the second end portion 176 being aligned with one another, shows the position of the second end wall portion 168 being adjacent the anterior edges of the lower vertebral body $V_1$ and the upper vertebral body $V_2$, and shows at the least the distances between the first end wall portion 138 and the first column 150, between the first column 150 and the second column 152, between the second column 152 and the third column 154 being smaller than the same distances along the mid-longitudinal axis $A_1$. These smaller distances in a lateral direction fluoroscopic image correlate to the angle of the mid-longitudinal axis $A_1$ with respect to the sagittal plane of the body. For example, when the distances in a lateral direction fluoroscopic image between at least the first end wall portion 138 and the first column 150, between the first column 150 and the second column 152, and between the second column 152 and the third column 154 are smaller than the same distances along the mid-longitudinal axis $A_1$, the mid-longitudinal axis $A_1$ (and the spinal implant trial 110) is at an acute angle with respect to the sagittal plane. The smaller the distances, the greater acute angle of the mid-longitudinal axis $A_1$ with respect to the sagittal plane.

Furthermore, when properly located/oriented, the anterior-posterior fluoroscopic representation depicted in FIG. 10 at the very least shows the position of the tip of the nose portion 186 spaced slightly apart from the spinous process $S_2$, shows the spinous process $S_2$ between the first end portion 174 and the second end portion 176, shows the first column 150, the second column 152, and the third column 154 being positioned on an opposite side of the spinous process $S_2$ from the nose portion 186, and shows the position of the end portion 130 being spaced apart from the lateral edges of the lower vertebral body $V_1$ and the upper vertebral body $V_2$.

Deviations from the proper location/orientation of the spinal implant 110 can be corrected using the above-discussed features of the spinal implant trial 110 to guide the corrections.

FIG. 12 is a representation of a fluoroscopic image taken of the spinal implant trial 110 as positioned in the disc space as shown in FIG. 11 from the lateral direction. FIG. 12 shows that the spinal implant trial 110 is properly located/oriented for a PLIF procedure within the disc space between the lower vertebral body $V_1$ and the upper vertebral body $V_2$.

When properly located/oriented, the lateral direction fluoroscopic representation depicted in FIG. 12 at the very least shows the position of the nose portion 186 being adjacent the anterior edges of the lower vertebral body $V_1$ and the upper vertebral body $V_2$, and shows at the least the distances between the first end wall portion 138 and the first column 150, between the first column 150 and the second column 152, and between the second column 152 and the third column 154 being directly proportional to the same distances along the mid-longitudinal axis $A_1$. These directly proportional distances indicate that the mid-longitudinal axis $A_1$ (and the spinal implant trial 110) is substantially aligned with the sagittal plane.

Deviations from the proper location/orientation of the spinal implant 110 can be corrected using the above-discussed features of the spinal implant trial 110 to guide the corrections.

While the spinal implant trial 110 is depicted in FIGS. 8-12, the spinal implant trial 10 can be used in a similar manner. Furthermore, while the spinal implant trials 10 and 110 can be inserted into the disc space from posterolateral (FIGS. 8-10) and posterior (FIGS. 11 and 12) directions, the spinal implant trials 10 and 110 can also be inserted into the disc space from anterior, anterolateral, and lateral directions. By properly locating/orienting the spinal implant trials 10 and 110 in the disc space, an appropriately configured and sized spinal implant or spinal implants, as well as ideal position in the disc space and implantation trajectory of the spinal implant or spinal implants, can be selected.

Figure 13:
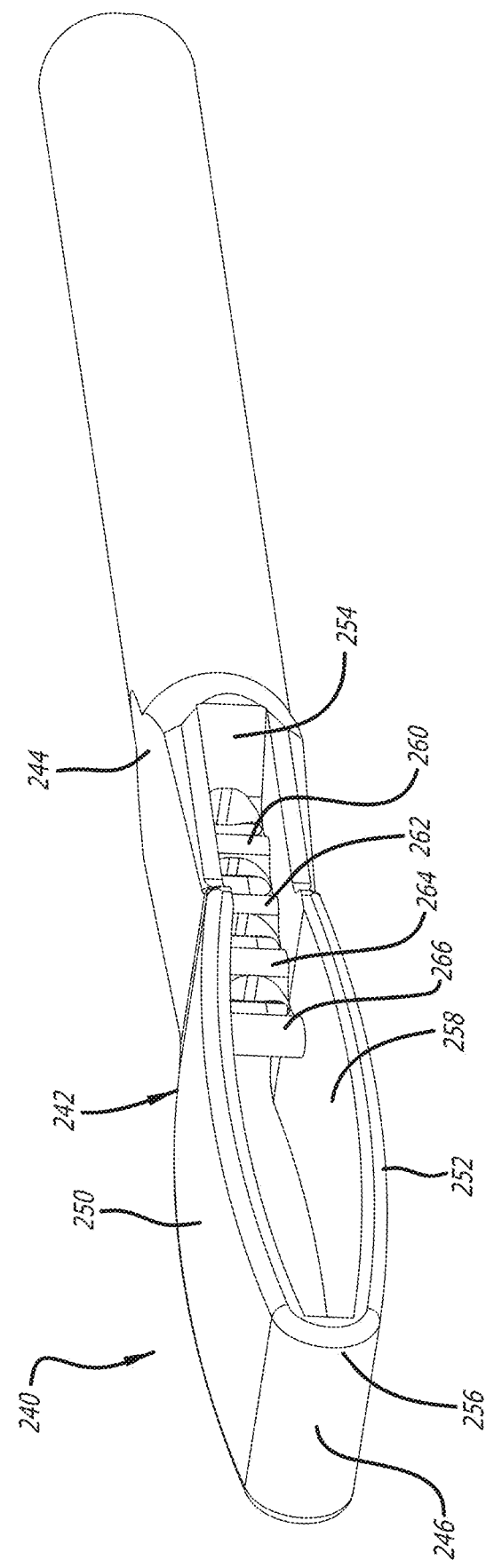
FIG. 13 is top side perspective view of a spinal implant trial according to a third embodiment of the present invention.

The spinal implant trial 240 can also be used in a similar manner as the spinal implant trials 10 and 110. Furthermore, as depicted in FIG. 13, the spinal implant trial 240 has similar features as the spinal implant trials 10 and 110. The spinal implant trial 240 includes a body portion 242 including a first end 244, an opposite second end 246, and a mid-longitudinal axis $A_5$ extending through the first end 244 and the second end 246. The first end 244 is the trailing end of the spinal implant trial 240 and the second end 246 is the leading end of the spinal implant trial 240.

The body portion 242 includes an upper wall portion 250 extending between the first end 244 and the second end 246, and includes a lower wall portion 252 extending between the first end 244 and the second end 246. The upper wall portion 250 and the lower wall portion 252, as well as a first end wall portion 254 and a second end wall portion 256, define an interior 258. The interior 258 includes one or more columns. and, for example, the spinal implant trial 240 a first column 260, a second column 262, a third column 264, and a fourth column 266. The first column 260, the second column 262, the column 264, and the fourth column 266 can be used in the same manner as the columns of the spinal implant trials 10 and 110.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of situating a spinal implant trial, the method comprising:

providing a spinal implant trial having a proximal first end, a distal second end, a body portion, and a head portion, the body portion extending from the proximal first end to the head portion, and the head portion extending from the body portion to the distal second end, the body portion including a first end collocated with the proximal first end of the spinal implant trial, an opposite second end, a first mid-longitudinal axis extending through the first end and the second end of the body portion, a first end wall portion positioned at or adjacent the first end of the body portion, an upper wall portion extending between the first end and the second end of the body portion, a lower wall portion extending between the first end and the second end of the body portion, an interior portion that is open along a majority of a first lateral side and a second lateral side of the body portion, the interior portion being formed between a portion of the first end wall portion and portions of the upper wall portion and the lower wall portion of the body portion, and at least a first column and a second column provided in the interior portion, the first column and the second column being at least in part radio opaque, each of the first column and the second column extending from at least adjacent the upper wall portion of the body portion to at least adjacent the lower wall portion of the body portion, the first column and the second column being positioned along the first mid-longitudinal axis, and the head portion including a first end, an opposite second end collocated with the distal second end of the spinal implant trial, and a second end wall portion positioned at least adjacent the distal second end of the spinal implant trial;

inserting the spinal implant trial into a disc space between an upper vertebral body and a lower vertebral body to contact a portion of the upper wall portion with a lower endplate of the upper vertebral body and to contact a portion of the lower wall portion with an upper endplate of the lower vertebral body; and locating and orientating the spinal implant trial in a first location and orientation so that a horizontal first distance between the first end wall portion and the first column in a first fluoroscopic image from a direct lateral direction, and a horizontal second distance between the first column and the second column in the first fluoroscopic image are respectively proportional to a third distance between the first end wall portion and the first column, and a fourth distance between the first column and the second column along the first mid-longitudinal axis.

2. The method of claim 1, further comprising relocating and reorienting the spinal implant trial in a second location and orientation so that a horizontal fifth distance between the first end wall portion and the first column in a second fluoroscopic image from the direct lateral direction, and a horizontal sixth distance between the first column and the second column in the second fluoroscopic image are respectively less than the horizontal first distance and the horizontal second distance.

3. The method of claim 2, further comprising relocating and reorienting the spinal implant trial in a third location and orientation so that a horizontal seventh distance between the first end wall portion and the first column in a third fluoroscopic image from the direct lateral direction, and a horizontal eighth distance between the first column and the second column in the third fluoroscopic image are respectively less than the horizontal fifth distance and the horizontal sixth distance.

4. The method of claim 3, wherein a sagittal plane extends through the upper vertebral body and the lower vertebral body, and wherein, when the spinal implant trial is in the second location, the first mid-longitudinal axis is oriented at a first acute angle with respect to the sagittal plane, and when the spinal implant trial is in the third location, the first mid-longitudinal axis is oriented at a second acute angle with respect to the sagittal plane, the second acute angle between the mid-longitudinal axis and the sagittal plane being greater than the first acute angle between the mid-longitudinal axis and the sagittal plane.

5. The method of claim 1, further comprising, after properly locating and orienting the spinal implant trial in the disc space, selecting a spinal implant to fit in the disc space, the selected spinal implant having one of a length approximating a first distance along the first mid-longitudinal axis between a first plane perpendicular to the first mid-longitudinal axis provided at the distal second end and a second plane perpendicular to the first mid-longitudinal axis extending through a middle of the first column, and a length approximating a second distance along the first mid-longitudinal axis between the first plane and a third plane perpendicular to the mid-longitudinal axis extending through a middle of the second column.

6. The method of claim 1, wherein the head portion includes a second mid-longitudinal axis extending through the first end and the second end thereof, and the second end wall portion extends between a first end portion and a second end portion, the first end portion and the second end portion being spaced apart from one another, the first end portion of the second end wall portion being positioned proximate the first end of the head portion and the second end portion of the second end wall portion being positioned proximate the second end of the head portion, the first end portion and the second end portion of the second end wall portion each having a thickness greater than remaining portion of the second end wall portion and being at least in part radio opaque.

7. The method of claim 6, wherein the first mid-longitudinal axis and the second mid-longitudinal axis are transverse to one another, the upper wall portion and the lower wall portion each include a first side surface extending at least partially in a third plane parallel to the first mid-longitudinal axis, and the upper wall portion and the lower wall portion each include a second side surface extending at least partially in a fourth plane parallel to the first mid-longitudinal axis, the body portion residing between the third plane and the fourth plane, and a portion of the head portion being located on an opposite side of the third plane from the body portion.

8. The method of claim 7, further comprising relocating and reorienting the spinal implant trial so that the first end portion and the second end portion of the second end wall portion are substantially aligned with one another from the direct lateral direction.

9. The method of claim 8, further comprising relocating and reorienting the spinal implant trial so that the first end portion and the second end portion of the second end wall portion are positioned on opposite sides of a sagittal plane extending through the upper vertebral body and the lower vertebral body.

10. A method of situating a spinal implant trial, the method comprising:
    inserting a spinal implant trial from an at least partially posterior direction into a disc space between an upper vertebral body and a lower vertebral body, the spinal implant trial including a proximal first end, a distal second end, a body portion, and a head portion, the body portion having at least a first end collocated with the proximal first end of the spinal implant trial, an opposite second end, a mid-longitudinal axis extending through the first end and the second end, an upper wall portion, a lower wall portion, a first end wall portion at or adjacent the first end of the body portion, and an interior portion extending therethrough that is open along a majority of a first lateral side and a second lateral side of the body portion, the interior portion being interrupted by a first column and a second column, and defined by at least the upper wall portion, the lower wall portion, and the first end wall portion, the first column and the second column each being at least in part radio opaque, the first column and the second column being spaced apart from one another along the mid-longitudinal axis, and the head portion including at least a second end wall portion at and adjacent the distal second end of the spinal implant trial;
    contacting the upper wall portion of the body portion of the spinal implant trial with a lower end portion of the upper vertebral body and contacting the lower wall portion of the body portion of the spinal implant trial with an upper end portion of the lower vertebral body;
    positioning the spinal implant trial in a first location and orientation within the disc space such that the spinal implant trial is on only one side of a sagittal plane dividing the disc space into a right lateral side and a left lateral side;
    producing a first fluoroscopic image from a direct lateral direction of the spinal implant trial in the first location and orientation within the disc space;
    determining if a horizontal first distance between the first end wall portion and the first column in the first fluoroscopic image, and a horizontal second distance between the first column and the second column in the first fluoroscopic image are respectively proportional to a third distance between the first end wall portion and the first column, and a fourth distance between the first column and the second column along the mid-longitudinal axis;
    further positioning the spinal implant trial in a second location and orientation within the disc space such that the spinal implant trial is on only one side of a sagittal plane extending through the upper vertebral body and the lower vertebral body;
    further producing a second fluoroscopic image from the direct lateral direction of the spinal implant trial in the second location orientation within the disc space; and
    further determining if a horizontal fifth distance between the first end wall portion and the first column in the second fluoroscopic image, and a horizontal sixth distance between the first column and the second column in the second fluoroscopic image are respectively proportional to the third distance and the fourth distance.

11. The method of claim 10, further comprising repeating the further positioning, the further producing, and the further determining until a horizontal seventh distance between the first end wall portion and the first column in a further fluoroscopic image from the direct lateral direction, and a horizontal eighth distance between the first column and the second column in the further fluoroscopic image are respectively proportional to the third distance and the fourth distance.

12. The method of claim 10, further comprising, after properly positioning the spinal implant trial in the disc space, selecting a spinal implant to fit in the disc space, the selected spinal implant having one of a length approximating a first distance along the mid-longitudinal axis between a first plane perpendicular to the mid-longitudinal axis provided at the distal second end and a second plane perpendicular to the mid-longitudinal axis extending through a middle of the first column, and a length approximating a second distance along the mid-longitudinal axis between the first plane and a third plane perpendicular to the mid-longitudinal axis extending through a middle of the second column.

13. The method of claim 10, wherein the mid-longitudinal axis is a first mid-longitudinal axis, and wherein the head portion includes a second mid-longitudinal axis extending through the first end and the second end thereof, and the second end wall portion extends between a first end portion and a second end portion, the first end portion and the second end portion being spaced apart from one another, the first end portion of the second end wall portion being positioned proximate the first end of the head portion and the second end portion of the second end wall portion being positioned proximate the second end of the head portion, the first end portion and the second end portion of the second end wall portion each having a thickness greater than a remaining portion of the second end wall portion and being at least in part radio opaque.

14. The method of claim 13, wherein the first mid-longitudinal axis and the second mid-longitudinal axis are transverse to one another, the upper wall portion and the lower wall portion each include a first side surface extending at least partially in a third plane parallel to the first mid-longitudinal axis, and the upper wall portion and the lower wall portion each include a second side surface extending at least partially in a fourth plane parallel to the first mid-longitudinal axis, the body portion residing between the third plane and the fourth plane, and a portion of the head portion being located on an opposite side of the third plane from the body portion.

15. The method of claim 13, further comprising relocating and reorienting the spinal implant trial so that the first end portion and the second end portion of the second end wall portion are substantially aligned with one another from the direct lateral direction.

16. The method of claim 13, further comprising relocating and reorienting the spinal implant trial so that the first end portion and the second end portion of the second end wall portion are positioned on opposite sides of the sagittal plane.

17. A method of situating a spinal implant trial, the method comprising:

inserting a spinal implant trial from an at least partially posterior direction into a disc space between an upper vertebral body and a lower vertebral body, the spinal implant trial including a proximal first end, a distal second end, and a body portion, the body portion having at least a first end collocated with the proximal first end of the spinal implant trial, an opposite second end, a mid-longitudinal axis extending through the first end and the second end, an upper wall portion, a lower wall portion, a first end wall portion at or adjacent the first end of the body portion, and an interior portion extending therethrough that is open along a majority of a first lateral side and a second lateral side of the body portion, the interior portion being interrupted by a first column and a second column, and defined by at least the upper wall portion, the lower wall portion, and the first end wall portion, the first column and the second column each being at least in part radio opaque, and the first column and the second column being spaced apart from one another along the mid-longitudinal axis;

contacting the upper wall portion of the body portion of the spinal implant trial with a lower end portion of the upper vertebral body and contacting the lower wall portion of the body portion of the spinal implant trial with an upper end portion of the lower vertebral body;

positioning the spinal implant trial in a first location and orientation within the disc space such that the spinal implant trial is on only one side of a sagittal plane dividing the disc space into a right lateral side and a left lateral side;

producing a first fluoroscopic image from a direct lateral direction of the spinal implant trial in the first location and orientation within the disc space; and determining if a horizontal first distance between the first end wall portion and the first column in the first fluoroscopic image, and a horizontal second distance between the first column and the second column in the first fluoroscopic image are respectively proportional to a third distance between the first end wall portion and the first column, and a fourth distance between the first column and the second column along the mid-longitudinal axis.

18. The method of claim 17, further comprising repeating the positioning, the producing, and the determining until a horizontal fifth distance between the first end wall portion and the first column in a further fluoroscopic image from the direct lateral direction, and a horizontal sixth distance between the first column and the second column in the further fluoroscopic image are respectively proportional to the third distance and the fourth distance.

19. The method of claim 18, further comprising, after properly positioning the spinal implant trial in the disc space, selecting a spinal implant to fit in the disc space, the selected spinal implant having one of a length approximating a first distance along the mid-longitudinal axis between a first plane perpendicular to the mid-longitudinal axis provided at the distal second end and a second plane perpendicular to the mid-longitudinal axis extending through a middle of the first column, and a length approximating a second distance along the mid-longitudinal axis between the first plane and a third plane perpendicular to the mid-longitudinal axis extending through a middle of the second column.

20. The method of claim 17, wherein at least a portion of the interior portion is filled with a radiolucent material, the radiolucent material-preventing tissue from entering the interior portion.

* * * * *